(12) United States Patent
Smith et al.

(10) Patent No.: US 9,743,661 B2
(45) Date of Patent: Aug. 29, 2017

(54) METHOD OF KILLING BEDBUG EGGS

(71) Applicant: Ecolab USA Inc., St. Paul, MN (US)

(72) Inventors: Kim R. Smith, Woodbury, MN (US); Erik C. Olson, Savage, MN (US); Yvonne M. Killeen, South St. Paul, MN (US); Victor F. Man, St. Paul, MN (US); Joelle F. Olson, Shoreview, MN (US); Erin F. Loosbrock, Eagan, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 13/682,348

(22) Filed: Nov. 20, 2012

(65) Prior Publication Data

US 2014/0142196 A1 May 22, 2014

(51) Int. Cl.
*A01N 31/02* (2006.01)

(52) U.S. Cl.
CPC .................................. *A01N 31/02* (2013.01)

(58) Field of Classification Search
CPC ....... C07C 43/123; C07C 43/12; A61K 31/08; A61K 9/0019; A01N 31/02
See application file for complete search history.

(56) References Cited

U.S. PATENT DOCUMENTS

| | | | | |
|---|---|---|---|---|
| 3,894,149 | A * | 7/1975 | Mast | 514/86 |
| 6,814,956 | B2 | 11/2004 | Besser et al. | |
| 2006/0112738 | A1* | 6/2006 | Worm et al. | 68/18 R |
| 2007/0254907 | A1 | 11/2007 | Bowles | |
| 2008/0261267 | A1* | 10/2008 | Ferrer et al. | 435/69.1 |
| 2008/0269177 | A1 | 10/2008 | Bessette | |
| 2008/0319029 | A1 | 12/2008 | Richman et al. | |
| 2009/0223115 | A1 | 9/2009 | Lang et al. | |
| 2010/0120652 | A1* | 5/2010 | Corrado | 510/319 |
| 2011/0256196 | A1* | 10/2011 | Lloyd et al. | 424/403 |

FOREIGN PATENT DOCUMENTS

| | | | |
|---|---|---|---|
| WO | WO 2009038599 A1 * | 3/2009 | |
| WO | WO2009/047584 A1 | 4/2009 | |
| WO | WO 2010126576 A1 * | 11/2010 | |
| WO | WO2013050967 A1 * | 4/2013 | ............. A01N 65/26 |

OTHER PUBLICATIONS

White, Bacterial Biodegradation of Ethoxylated Surfactants, Pesticide Science, 1993, 37, pp. 159-166.*
NCBI, Fatty Alcohols, http://www.ncbi.nlm.nih.gov/mesh/68005233, Uploaded Feb. 28, 2014.*
Pest Management Professional, *The Business of Bed Bugs*, Michael F. Potter, Jan. 1, 2008 (8 pages).
www.bed-bug.net, Bed Bug Killer/How to Kill Bed Bugs/Bed Bug Information, printed Apr. 13, 2010 (1 page).
Bayer Environmental Science, Need to Know, *Temprid® SC now labeled for Bed Bugs*, vol. 7, No. 1, Feb. 18, 2010.
Penn State University, Dept of Entomology, Entomological Notes, Bed Bugs, http://ento.psu.edu/extension/factsheets/bedbugs, printed Apr. 13, 2010 (4 pages).
MGK® Product Code 027911, Material Safety Data Sheet, Bedlam™ Insecticide, Feb. 28, 2006 (2 pages).
TARR Status Report, http://tarr.uspto.gov/, Serial No. 77771410, Registration No. 3751703, mark:Bedlam Insecticide, printed Apr. 12, 2010 (2 pages).
National Center for Healthy Housing, *What's Working for Bed Bug Control in Multifamily Housing: Reconciling best practices with research and the realities of implementation*, undated (3 pages cover page, table of contents, and p. 22).
FMC Corporation, *Best Management Practices*, Bed Bugs, 2009 (3 pages).
Snell, Eric J., Smith, Todd, Sexton, Wally, *Eclosion of Bed Bug (Cimex Lectularius) Eggs after Exposure to Various Compounds*, Snell Scientifics LLC, Meansville, GA, submitted paper at the National Conference on Urban Entomology in Tulsa, OK, May 18-21, 2008 (1 page).

* cited by examiner

*Primary Examiner* — San-Ming Hui
*Assistant Examiner* — Andrew Lee
(74) *Attorney, Agent, or Firm* — Merchant & Gould P.C.

(57) ABSTRACT

The present invention relates to a method of pre-rinsing laundry and treating other surfaces employing a composition that can kill bedbug eggs. The composition includes a fatty alcohol and an alcohol ethoxylate.

14 Claims, No Drawings

METHOD OF KILLING BEDBUG EGGS

FIELD OF THE INVENTION

The present invention relates to a method of pre-rinsing laundry and treating other surfaces employing a composition that can kill bedbug eggs. The composition includes a fatty alcohol and an alcohol ethoxylate.

BACKGROUND OF THE INVENTION

The occurrence of bedbugs or other insect pests in textiles or surfaces in areas occupied by people has increased recently. And, such removal of such pests may require pesticides of undesirable toxicity. Bedbugs are relatively small insects, approximately ¼ inch long and less than ¼ inch wide that feed on the blood of animals, including humans. And, their eggs are even smaller, about the size of a dust spec. When first laid, the eggs are sticky causing them to adhere to surfaces. Thus, they can be difficult to find in and on textiles (e.g., laundry).

Some believe that exposing textiles (e.g., laundry) to the heat of drying in a laundry dryer is sufficient to kill bedbugs and bedbug eggs in the textiles. However, due to uneven heat, too short exposure to the heat, and other factors, bedbugs and bedbug eggs often survive a trip through the dryer. Thus, there remains a need for additional methods and compositions for reducing the population of, killing, or reducing the viability of bedbugs and their eggs.

SUMMARY OF THE INVENTION

The present invention relates to a method of pre-rinsing laundry and treating other surfaces employing a composition that can kill bedbug eggs. The composition includes a fatty alcohol and an alcohol ethoxylate.

The present invention includes a method of pre-rinsing a textile suspected of contamination with a pest, such as a bedbug or bedbug egg. This method includes providing the textile suspected of contamination with a pest; pre-rinsing the textile with a composition comprising an effective pesticidal amount of a fatty alcohol and an alcohol ethoxylate. This composition is effective for reducing the viable population of bed bug eggs. The method can also include washing the textile.

The present invention includes a method of treating an article suspected of contamination with a pest. This method includes providing the article suspected of contamination with a pest and applying to the article a composition comprising an effective pesticidal amount of a fatty alcohol and an alcohol ethoxylate. This composition is effective for reducing the viable population of bed bug eggs.

DETAILED DESCRIPTION OF THE INVENTION

The present invention relates to a method of pre-rinsing laundry and treating other surfaces employing a composition that can kill bedbug eggs. The composition includes a fatty alcohol and an alcohol ethoxylate.

The present invention relates to methods employing a fatty alcohol and an alcohol ethoxylate as a safe and effective bedbug treatment, for example, in a textile (e.g., laundry) pre-rinse before use of detergent to wash the textile (e.g., laundry). The present pesticidal composition can be drained from the washing machine before the detergent is added. The present method is effective against bedbug eggs.

In an embodiment, the present invention includes a method of pre-rinsing a textile suspected of contamination with a pest, such as a bedbug or bedbug egg. This method can include providing the textile suspected of contamination with a pest. This method can also include pre-rinsing the textile with a composition comprising an effective pesticidal amount of a fatty alcohol and an alcohol ethoxylate. This composition is effective for reducing the viable population of (e.g., killing) bed bug eggs. The method can also include washing the textile, for example, with detergent in a subsequent step.

Textiles that can be treated with the method of the invention include, for example, clothing, bedding, a drape, a towel, a mattress, upholstery, or a combination thereof.

The composition can include any of a variety of fatty alcohols. Suitable fatty alcohols include $C_8$-$C_{18}$ fatty alcohols. In an embodiment, the fatty alcohol is a $C_{10}$-$C_{14}$ fatty alcohol. The composition can include any of a variety of alcohol ethoxylates. Suitable alcohol ethoxylates have a carbon chain length of about 8 to about 18 and about 6 to about 12 ethoxylate groups. Suitable alcohol ethoxylates include biodegradable alcohol ethoxylates.

Suitable alcohol ethoxylates include those that are water soluble with an HLB of 12 or more and a cloud point of about 70° F. or higher. Suitable alcohol ethoxylates include linear alcohol ethoxylates. Suitable alcohol ethoxylates include branched alcohol ethoxylates. Although not limiting to the present invention, it is believed that in certain embodiments, the alcohol ethoxylate emulsifies the fatty alcohol in the composition.

In an embodiment, the composition includes a fatty alcohol and an alcohol ethoxylate. The fatty alcohol and alcohol ethoxylate can be in any of a variety of weight ratios in the compositions. Suitable weight ratios of fatty alcohol to alcohol ethoxylate include about 1:5 to about 5:1. Suitable weight ratios of fatty alcohol to alcohol ethoxylate include about 1:1 or 1:1.

In an embodiment, the effective pesticidal amount of anionic compound is about 0.1 wt-% to about 3 wt-%.

In an embodiment, the composition also includes water and, optionally, dye and fragrance. In an embodiment, the composition includes an enzyme. Suitable enzymes include lipase, cellulase, protease, pectinase, amylase, or a mixture thereof.

In an embodiment, the composition is pesticidal against cockroach, bed bug, ant, fly, termite, or mixture thereof.

The present invention also includes a method of treating an article suspected of contamination with a pest, such as a bedbug or bedbug egg. This method can include providing the article suspected of contamination with a pest. This method can include applying to the article a composition comprising an effective pesticidal amount of a fatty alcohol and an alcohol ethoxylate. This composition is effective for reducing the viable population of bed bug eggs. Suitable articles include, for example, a hard surface selected from the group consisting of a floor, a ceiling, a window, a wall, and a combination thereof.

Alcohol Ethoxylates

Suitable alcohol ethoxylates include alkyl ethoxylate condensation products of aliphatic alcohols with from about 0 to about 25 moles of ethylene oxide. The alkyl chain of the aliphatic alcohol can either be straight or branched, primary or secondary, and generally contains from 6 to 22 carbon atoms. Additional suitable alcohol ethoxylates include the ethoxylated $C_6$-$C_{18}$ fatty alcohols and $C_6$-$C_{18}$ mixed ethoxylated and propoxylated fatty alcohols. Suitable ethoxylated fatty alcohols include the $C_{10}$-$C_{18}$ ethoxylated fatty alcohols with a degree of ethoxylation of from 3 to 50.

The present invention may be better understood with reference to the following examples. These examples are intended to be representative of specific embodiments of the invention, and are not intended as limiting the scope of the invention.

Example—Treating Bedbug Eggs with Alcohol and Alcohol Ethoxylate

Several aqueous test compositions were prepared for testing. Bedbug eggs were then contacted with a 100° F. test composition for 5 min.

| Test Composition | % Kill of Bedbug Eggs | % Kill of Bedbug Eggs and Nymphs |
|---|---|---|
| 1% decanol, 1% Surfonic 12-6 | 100 | 100 |
| 1% lauryl alcohol, 1% Surfonic 12-6 | 45 | 65 |
| 1% tetradecyl alcohol, 1% Surfonic 12-6 | 75 | 80 |
| 1% decanol, 1% Surfonic 24-7 | 85 | 90 |
| 1% decanol, 1% Surfonic 12-12 | 80 | 100 |

Surfonic 12-6 is a decyl/lauryl alcohol ethoxylate with 6 EO available from Huntsman Chemical. Surfonic 24-7 is a lauryl/myristyl alcohol ethoxylate with 7 EO available from Huntsman Chemical.

Compositions including hypochlorite exhibited reduced kill compared to the corresponding composition without hypochlorite. Although not limiting to the present invention, it is believed that in some circumstances hypochlorite bleach increases resistance of bedbug eggs to pesticides.

Kill was not affected by adding to the composition hydrogen peroxide or an enzyme such as lipase, cellulase, protease, pectinase, amylase, or a mixture thereof As used herein, weight percent (wt-%), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method of treating a textile suspected of contamination with a pest, the method consisting of:
    pre-rinsing the textile with an aqueous composition consisting essentially of water, a pesticide component, and optionally one or more of an enzyme, a dye, or a fragrance, wherein pesticide components used during the pre-rinsing consist of an effective pesticidal amount of a fatty alcohol comprising 8-18 carbon atoms and an alcohol ethoxylate, and wherein the aqueous composition is effective for reducing the viable population of bed bug eggs;
    draining the aqueous composition; and
    washing the textile in a second aqueous composition.

2. The method of claim 1, wherein the textile comprises clothing, bedding, a drape, a towel, a mattress, upholstery, or a combination thereof.

3. The method of claim 1, wherein the composition is pesticidal against cockroach, bed bug, bed bug egg, ant, fly, termite, or mixture thereof.

4. The method of claim 1, wherein the fatty alcohol comprises 10 to 14 carbon atoms.

5. The method of claim 1, wherein the alcohol ethoxylate has a carbon chain length of about 8 to about 18 and about 6 to about 12 ethoxylate groups.

6. The method of claim 5, wherein the alcohol ethoxylate is biodegradable.

7. The method of claim 1, wherein the ratio of fatty alcohol to alcohol ethoxylate is about 1:5 to about 5:1.

8. The method of claim 7, wherein the ratio of fatty alcohol to alcohol ethoxylate is about 1:1.

9. The method of claim 1, wherein the enzyme is selected from lipase, cellulase, protease, pectinase, amylase, or a mixture thereof.

10. The method of claim 1, wherein the effective pesticidal amount is concentration of about 0.1 wt-% to about 3 wt-%.

11. A method of treating an article suspected of contamination with a pest, the method consisting of:
    applying to the article an aqueous composition consisting essentially of water, a pesticide component, and optionally one or more of an enzyme, a dye, or a fragrance, wherein pesticide components applied during the method consist of about 0.1 wt-% to about 3 wt-% of a fatty alcohol comprising 8-18 carbon atoms and an alcohol ethoxylate;
    wherein the composition is effective for reducing the viable population of bed bug eggs.

12. The method of claim 11, wherein the article comprises a hard surface selected from the group consisting of a floor, a ceiling, a window, a wall, and a combination thereof.

13. The method of claim 1, wherein the pesticide component consists of:
    1 wt-% decanol, lauryl alcohol, or tetradecyl alcohol; and
    1 wt-% of a decyl/lauryl alcohol ethoxylate with 6 EO or a lauryl/myristyl alcohol ethoxylate with 7 EO.

14. The method of claim 11, wherein the pesticide component consists of:
    1 wt-% decanol, lauryl alcohol, or tetradecyl alcohol; and 1 wt-% of a decyl/lauryl alcohol ethoxylate with 6 EO or a lauryl/myristyl alcohol ethoxylate with 7 EO.

\* \* \* \* \*